(12) United States Patent
Spaide

(10) Patent No.: US 8,491,124 B2
(45) Date of Patent: Jul. 23, 2013

(54) SYSTEMS AND METHODS FOR WIDEFIELD MAPPING OF THE RETINA

(71) Applicant: Richard R. Spaide, New York, NY (US)

(72) Inventor: Richard R. Spaide, New York, NY (US)

( * ) Notice: Subject to any disclaimer, the term of this patent is extended or adjusted under 35 U.S.C. 154(b) by 0 days.

(21) Appl. No.: 13/718,123

(22) Filed: Dec. 18, 2012

(65) Prior Publication Data

US 2013/0107210 A1    May 2, 2013

Related U.S. Application Data

(63) Continuation of application No. 13/042,026, filed on Mar. 7, 2011, now Pat. No. 8,356,901.

(60) Provisional application No. 61/310,836, filed on Mar. 5, 2010.

(51) Int. Cl.
*A61B 3/00* (2006.01)
*A61B 3/14* (2006.01)

(52) U.S. Cl.
CPC ........................................ *A61B 3/14* (2013.01)
USPC ............................ 351/246; 351/206; 351/221

(58) Field of Classification Search
CPC ........................................................ A61B 3/14
USPC ................... 351/200, 205, 206, 210, 221, 246
See application file for complete search history.

(56) References Cited

U.S. PATENT DOCUMENTS 7,637,617 B2 * 12/2009 Liu et al. ........................ 351/221
8,356,901 B2 * 1/2013 Spaide ........................... 351/246

* cited by examiner

*Primary Examiner* — Huy K Mai
(74) *Attorney, Agent, or Firm* — Ronald Abramson; Hughes Hubbard & Reed LLP

(57) ABSTRACT

Systems and methods for constructing a widefield image of the retina from a plurality of retinal images. In one aspect, the disclosure concerns constructing a widefield image of the retina from a plurality of retinal images, comprising a base image and a plurality of peripheral images. These techniques enable medical observations of retinal phenomena in patients, such retinal vein occlusion, artery occlusion, retinal detachments, intraocular inflammation, ocular tumors, and the like, that were difficult to detect and impossible to quantify under prior art approaches.

17 Claims, 6 Drawing Sheets

A

B

SYSTEMS AND METHODS FOR WIDEFIELD MAPPING OF THE RETINA

CROSS REFERENCE TO RELATED APPLICATIONS

This application claims priority to U.S. Non-provisional patent application Ser. No. 13/042,026 filed Mar. 7, 2011 which claims priority to U.S. Provisional Patent Application Ser. No. 61/310,836, filed Mar. 5, 2010, the disclosures of which are hereby incorporated by reference in their entirety.

BACKGROUND OF THE DISCLOSED SUBJECT MATTER

1. Field of the Disclosed Subject Matter

The disclosed subject matter is in the field of the ophthalmology, more particularly, diagnostic retinal imaging, for example, of retinal circulation, and concerns systems and methods for constructing a widefield image of the retina from a plurality of retinal images, comprising a base image and a plurality of peripheral images. The techniques disclosed herein enable medical observations of retinal phenomena in patients, such as retinal vein occlusion, artery occlusion, retinal detachments, intraocular inflammation, ocular tumors, and the like, which were difficult to detect and impossible to quantify under prior art approaches.

2. Description of Related Art

Imaging of the retinal circulation has principally been done with fluorescein angiography in which the image is typically recorded with a fundus camera or a scanning laser ophthalmoscope. With a fundus camera the peripheral portion of an objective lens is used to focus light to illuminate the fundus and the central portion of the objective lens is used to create a real, inverted image of the fundus within the body of the camera. Additional optical elements are used to project the real image onto the imaging plane. The scanning laser ophthalmoscope uses a rotating mirror system to steer laser illumination across the fundus and an objective lens is used to gather the reflected light. The field of view of commercial fundus cameras ranges from 30 to 60 degrees and from commercial scanning laser ophthalmoscopic systems from 10 to 30 degrees. Shifting the axis of either of these devices allows observation of more peripheral portions of the patient's eye, but with decreasing image quality secondary to decreasing width of the entrance pupil, vignetting, and induced astigmatism.

One approach that has been used to overcome limitations inherent in conventional lens based systems with coaxial illumination, is the use of a widefield imaging system based on an ellipsoidal mirror. See Anderson, D C, Lucas, R A, Henderson, R. U.S. Pat. No. 5,815,242 ("Wide Field Scanning Laser Opthalmoscope [sic]"), incorporated herein by reference. The approach of Anderson, et al. is illustrated in FIG. 1 hereto. Elliptical mirrors have two conjugate focus points (FIG. 1A); extending this idea to three dimensions by rotating the ellipse would create an ellipsoidal surface capable of focusing light rays emanating from the eye (FIG. 1B). The retina is illuminated by a laser, the spot of which is scanned over the ellipsoidal surface to illuminate the conjugate point in the fundus. Using this technique, the Optos P200 Scanning Laser Ophthalmoscope (Optos North America, Marlborough, Mass.) has a stated field of view of 200 degrees.

SUMMARY OF THE DISCLOSED SUBJECT MATTER

The operation and advantages of the disclosed subject matter will be set forth in and apparent from the description that follows, and may be learned as well by practice of the disclosed subject matter.

In summary, the disclosure herein concerns systems and methods for retinal imaging, including for example imaging and mapping the retinal circulation, the retinal periphery, and evaluating the size and distribution of inflammatory lesions or intraocular tumors.

In one aspect, the disclosure concerns constructing a widefield image of the retina from a plurality of retinal images, comprising a base image and a plurality of peripheral images.

The techniques disclosed herein enable medical observations of retinal phenomena in patients, such as retinal vein occlusion, that were difficult to detect and impossible to quantify under prior art approaches.

Other aspects and advantages of the invention will be apparent from the accompanying drawings and the detailed description that follows.

BRIEF DESCRIPTION OF THE DRAWINGS

For a more complete understanding of the disclosed subject matter and the advantages thereof, reference is now made to the following description taken in conjunction with the accompanying drawings, wherein like reference numerals represent like parts, in which.

DETAILED DESCRIPTION OF THE PREFERRED EMBODIMENT

The following is a detailed description of certain embodiments of the invention chosen to provide illustrative examples of how it may preferably be implemented. The scope of the invention is not limited to the specific embodiments described in the following detailed description, nor is it limited by any specific implementation, embodiment or characterization depicted in the accompanying drawings or stated or described in the invention summary or the abstract. In addition, nothing contained in this written description should be understood to imply any necessary order of steps where processes are claimed, except as may be specified by express claim language.

Figure 1:
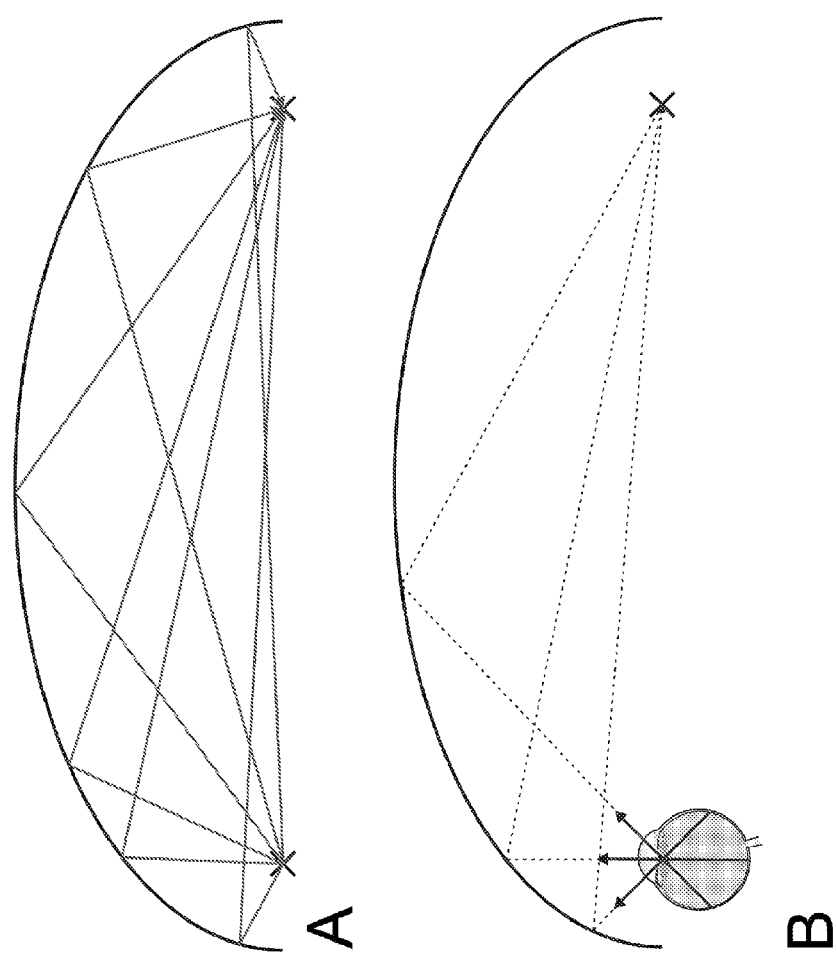
FIG. 1A schematically shows light paths in an elliptical mirror.
FIG. 1B schematically shows how an ellipsoidal surface may be used to reflect light from an illumination source three-dimensionally to scan the retina.
Figure 2:
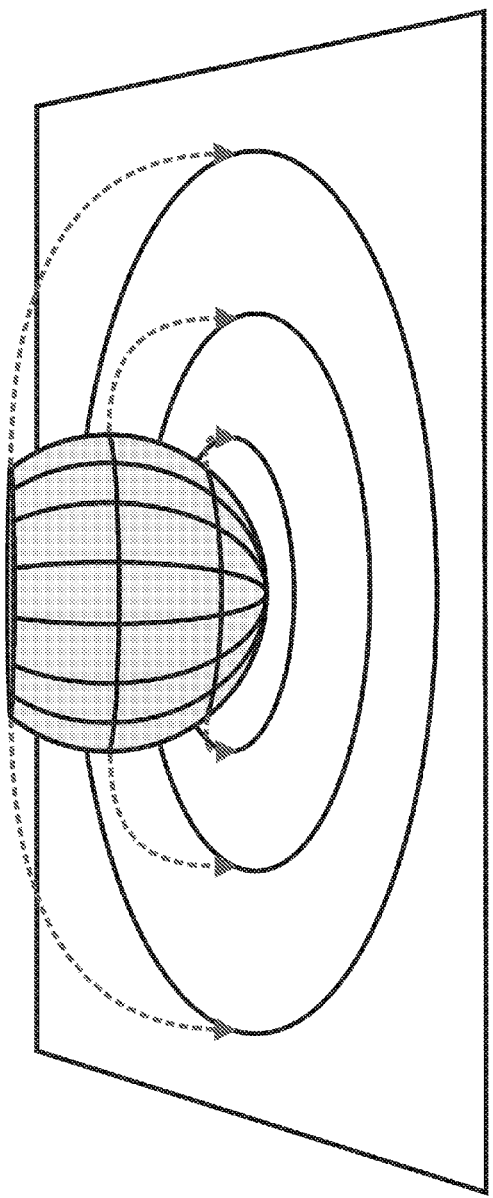
FIG. 2 schematically shows an azimuthal projection from a spherical structure, such as the eye, to a planar image.

Images made of the inner surface of the eye, which is nearly spherical, cannot be mapped to a flat surface without distortion as per Gauss. Although flat maps have numerous advantages over a globe, including being able to be represented on a computer monitor, it is not possible to create a flat map without inducing distortions; some attributes such as conformality, distance, direction, scale, or area may be preserved, but not all of them can be retained simultaneously. A fundus drawing creates a flat surface in which the radial distances of the drawing are proportional to the arc distance from the posterior pole. This produces an azimuthal projection (FIG. 2), in which distances and directions from the fovea, the center point of the eye, are retained. With further eccentricity from the center there are larger distortions of the size and shape of structures. There are a number of possible ways to make azimuthal projections (FIG. 3A (Orthographic), 3B (Stereographic), 3C (Gnomonic)). For nearly all of these techniques only a hemisphere is imaged, but for the retina it is common to continue anterior to the equator.

Figure 3:
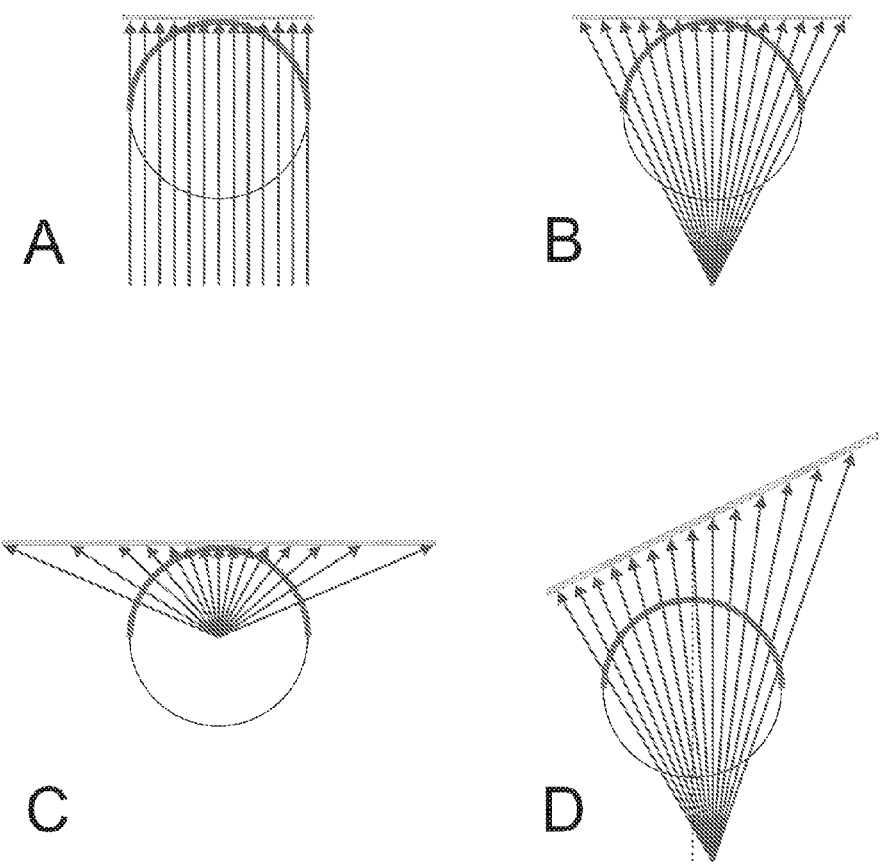
FIGS. 3A, 3B, and 3C schematically show, respectively, orthographic, stereographic, and Gnomonic methods for making azimuthal projections of a spherical structure.
FIG. 3D shows a distorted image due to shifting the axis of projection to the plane onto which the projection is made.

Although any one instrument cannot image the entire retina, it is possible to direct the gaze of the patient in cardinal direction to obtain images from additional areas of the eye. Component images show varying amounts of distortion and are not readily merged into one composite image. These images are not standardized to any particular axis of the eye and the projection plane is not rigorously defined. If the axis of the projection is shifted or the plane onto which the projection is made is shifted, the resultant projection induces additional distortions to the projected image (FIG. 3D). In clinical practice widefield imaging of the eye does not have fixed, precise, relationship with the imaging system, and varying deformations can be induced. Therefore, there can be a varying amount of image deformation in photographs taken of the eye, particularly in photographs of the more peripheral portions of the retina. This limits the potential for accurate measurements of sizes and areas of ocular structures and abnormalities.

Widefield imaging systems show obvious distortions because the larger field of view makes the image deformations more readily evident. Images taken with a fundus camera or conventional scanning laser ophthalmoscope have the same underlying problem, but the amount of image deformation in each picture is less evident because of the corresponding field of view is smaller. However, to obtain a widefield image using photographs from a fundus camera or scanning laser ophthalmoscope, a large number of images would have to be montaged.

Figure 4:
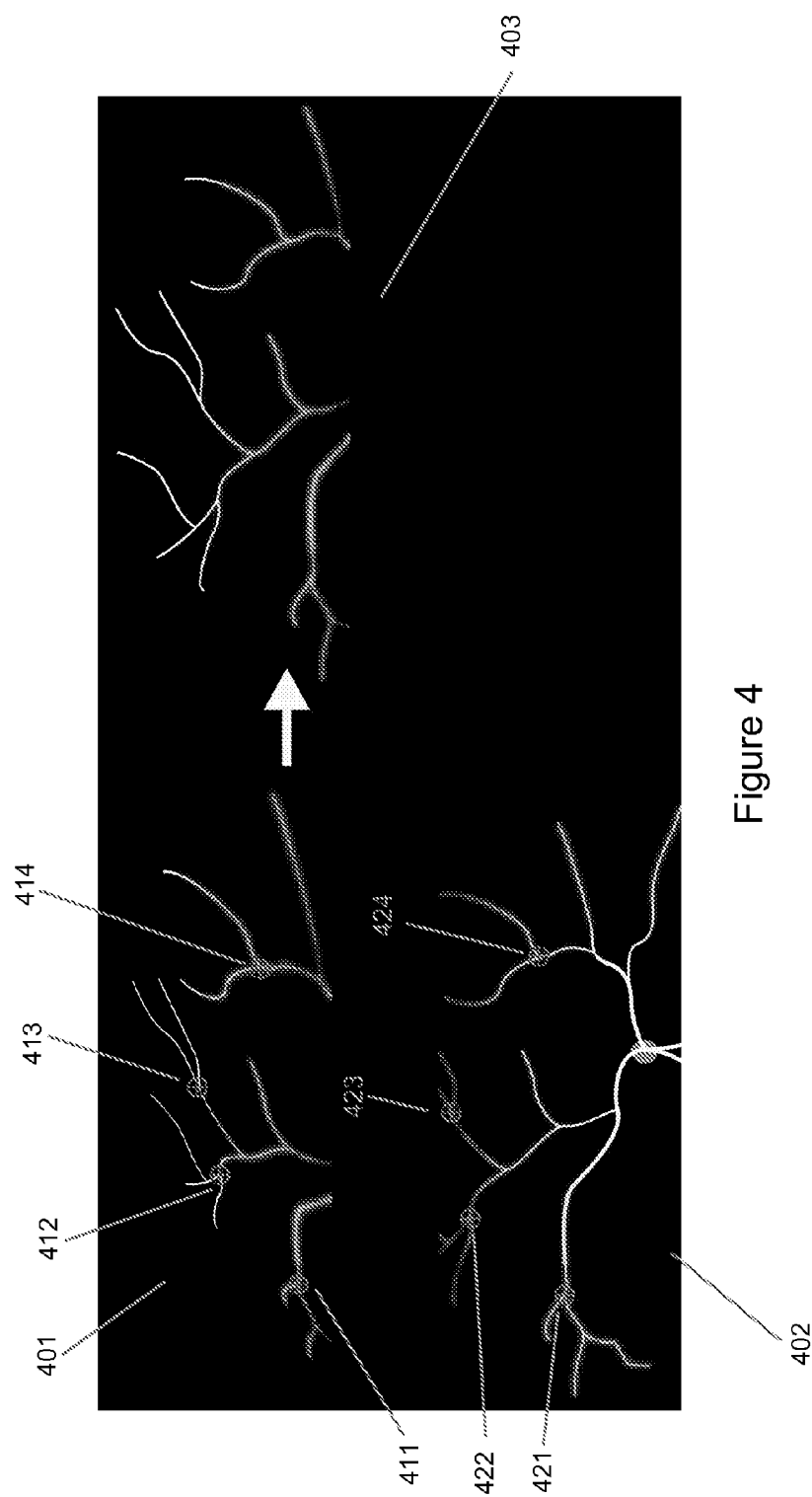
FIG. 4 shows base and output images made in accordance with one aspect of the disclosure.

In a manner similar to that used for generating fundus drawings, it should be possible to extend the azimuthal projection from the posterior of the eye by including the regions anterior to the equator of the eye. In such an approach, a widefield image is made, centered on the posterior portion of the eye. This image, for purposes of explanation, will be referred to as the base image. The images taken from the cardinal directions of the eye (the target images) may then be registered to the base image (FIG. 4). In one implementation, the registration would involve warping the peripheral images to match the distortion characteristics of the base image. In a further aspect of such an implementation, elastic image registration is performed, using control points selected in the base image and the target image. This can be a semi-automatic operation, or, when starting with widefield images may involve human intervention, because of the potential for large amounts of image distortion.

In FIG. 4 the upper left (401) represents a raw image acquired with a widefield imaging system. The upper portion of the base image is shown in the lower left (402). The control points (411-414 and 421-424) are shown in red. Using elastic warping of the upper image, it is made to match with the base image, producing the output in the upper right (403).

In one implementation, an image centered on the posterior portion of the eye, and a plurality of peripheral images, are taken. Preferably, these images should be sharp and without systemic distortion. Image artifacts from the lids, lashes and nose are removed from the images. The images are padded at their borders with additional black pixels.

Figure 5:
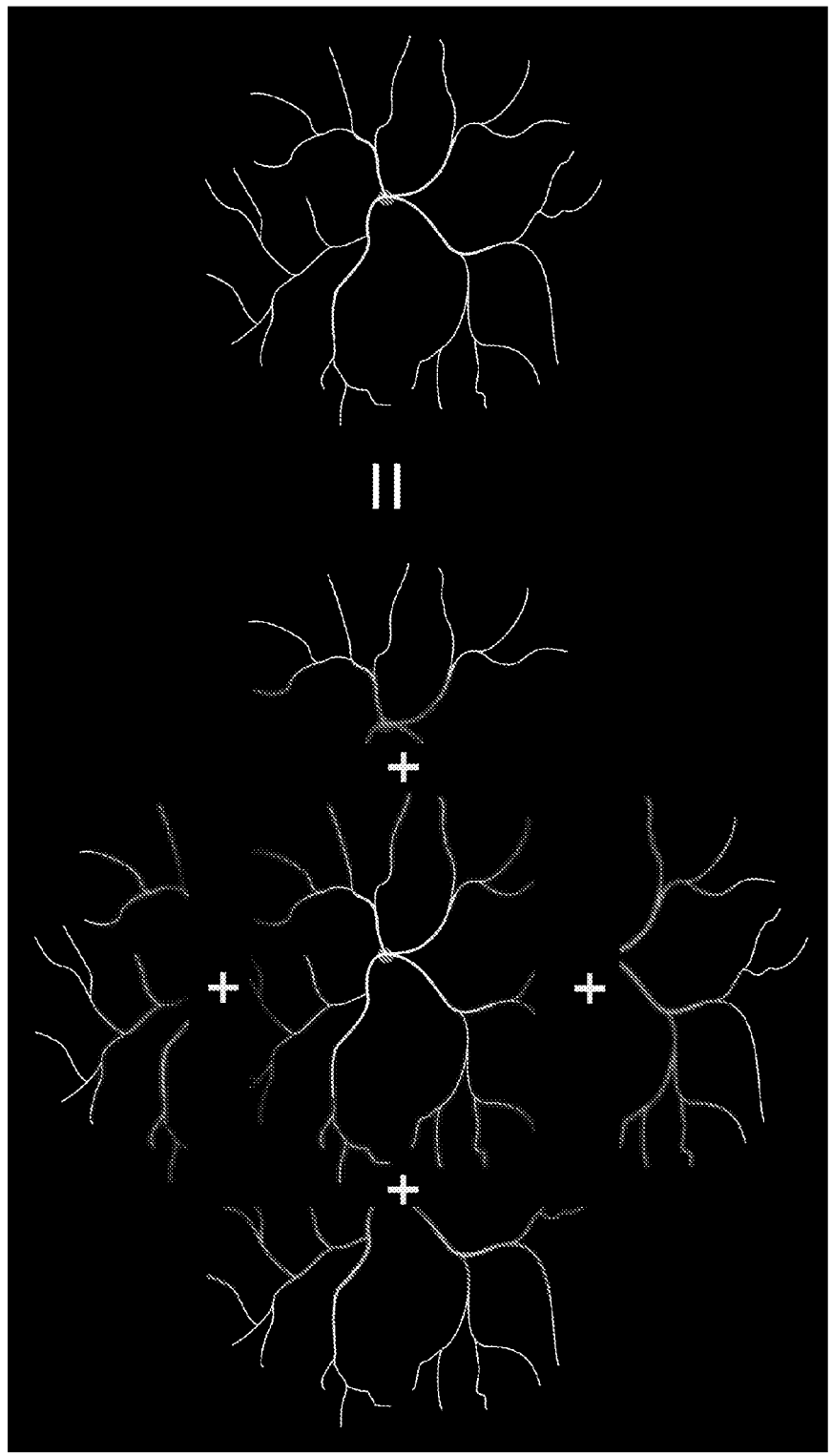
FIG. 5 shows a montage larger image made in accordance with one aspect of the disclosure.

The peripheral images (401) were transformed using elastic deformation so that the posterior portions of the peripheral images matched the base, reference image (402). Manual selection of control points (411-414 and 421-424) were used in each image pair and in each case the peripheral image was warped to fit the reference base image using a transformation, such as one employing thin-plate splines. These images are then montaged to form a larger image (FIG. 5).

Although this image has varying distortions of the peripheral images reduced and matched to the posterior base image, there are still opportunities for the merged image to deviate from actual linear correspondence to the retina itself.

To address the latter concern, inspection of the widefield color images and widefield fluorescein angiographic images was done to be able to identify the vortex vein ampullae, which are located at the ocular equator. These locations were plotted onto the montage (widefield) fluorescein angiograms. A generalized schematic generated from reported anatomic dimensions of the retina was created to be able to calculate the sizes of regions within the retinal image. The montage retinal photographs are then warped to fit the retinal drawing schematic using the known landmarks of the optic nerve, macula, and equator.

The reported sizes of the eye and distances between landmarks vary considerably. See Duke-Elder S. and Wybar K. C., The Anatomy of the Visual System, In: Duke-Elder, ed. System of Ophthalmology, Volume II. St. Louis: Mosby 1961, 220-271; Straatsma B. R., Landers M. B., Kreiger A. E., Apt L., Topography of the adult human retina, UCLA Forum Med Sci. 1969, 8:379-410; N. Drasdo and C. W. Fowler, Nonlinear projection of the retinal image in a wide-angle schematic eye, Br. J. Ophthalmol. 1974, 58:709-714; Taylor E., Jennings A., Calculation of total retinal area, Br. J. Ophthalmol. 1971, 55:262-5, each incorporated herein by reference. A simplified schematic eye model based on these references was developed using the following parameters: radius to retina, 11.1 mm, extension of the retina anterior to the equator: 5 mm. From this schematic anatomical model the calculated retinal surface area of the model was 1108 mm.sup.2, minus approximately 2 mm.sup.2 for the actual size of the optic disc yields 1106 mm.sup.2. This value is in fairly close agreement with the calculated surface area of 1065 mm.sup.2 by Drasdo and Fowler and 1132 mm.sup.2 by Taylor and Jennings The actual retinal surface area corresponds to the retinal drawing azimuthal area of 1590 mm.sup.2, reflecting the increasing distortion of retinal drawings as compared with the actual retinal surface area. (Of course the retinal drawing is made much larger because it is scaled.)

Over this schematic, ocular landmarks are plotted, including the optic nerve, macula, and equator. The montage angiogram with the known landmarks was then warped to fit the schematic. This created a projection of the retina to a topography similar to that used for retinal drawings that is therefore standardized from one patient to the next. As expected this projection stretches the periphery of the eye more than more posteriorly located areas. To measure areas of the mapped projection one of two main approaches can be taken. A software routine can make a transformation of the azimuthal projection image such that each pixel of the image corresponded to the same amount of retinal surface area. This, in effect, creates the equivalent of a Lambert azimuthal equal area projection from which areas of the retina are directly proportional to the number of pixels in the image of the retina. From the Lambert azimuthal equal area projection nonperfused areas of the retina can be measured. A second related approach is to use a software routine employing an algorithm that automatically applies a correction factor converting the area occupied by a pixel in the image to the actual corresponding area of the retina as a function of the radial distance from the center. This second approach is somewhat more computationally intensive, but allows the operator to use images with the familiar representation as they would appear on a retinal drawing form.

Figure 6:
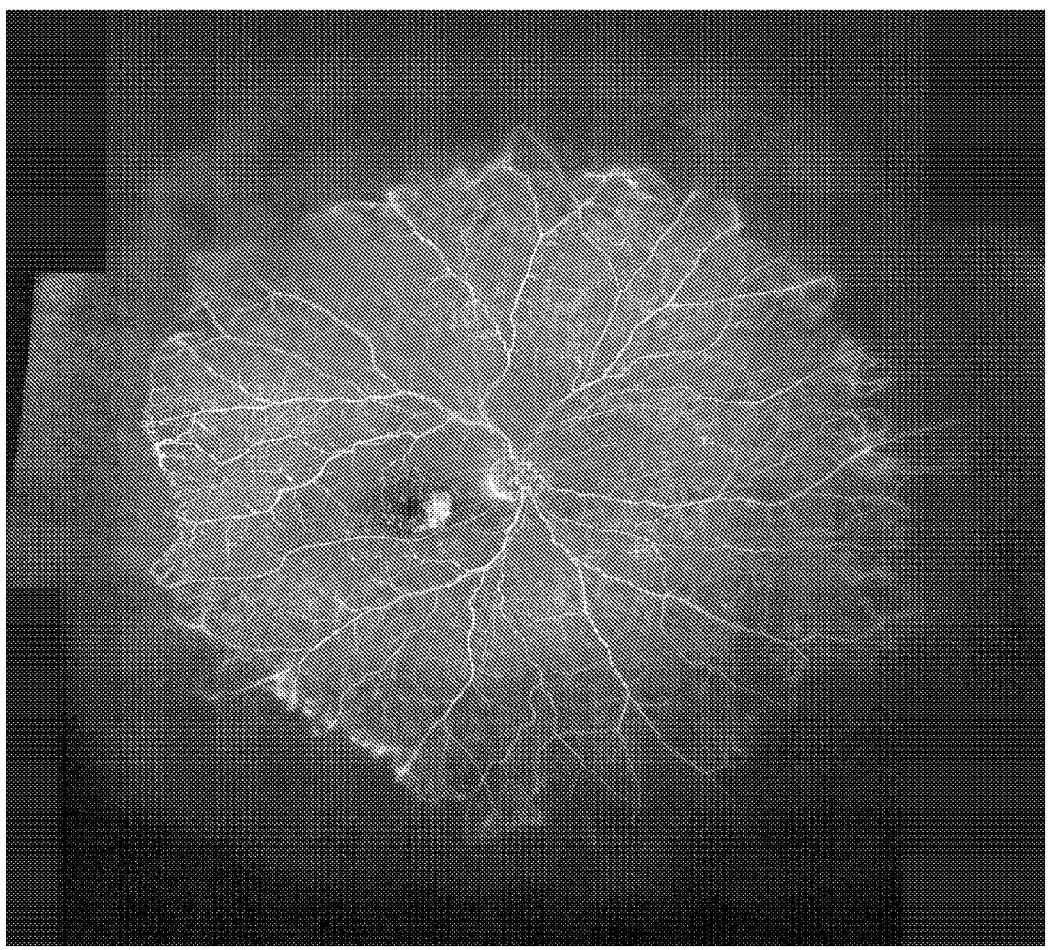
FIG. 6 shows a panretinal mapping of circulation, made in accordance with one aspect of the disclosure.

This imaging technique would provide very wide field images of the ocular fundus, allow assessment of the retinal circulation over its full extent, and give the opportunity for image measurement in regions not visible by other means. For example, a condition known as central retinal vein occlusion was thought to be due to an occlusion of the central retinal vein of the retina. By employing the methodologies explained above, a panretinal mapping of the circulation is revealed in FIG. 6.

This figure shows an image of the retina in which the entire extent of the retinal circulation is visible. The dark gray area surrounding the outer border of the vessels is actually where the circulation should also cover. Using this methodology, it was discovered that patients with central retinal vein occlusion also develop large areas of vascular occlusion in the more peripheral portions of their retinas. This new finding would have been difficult to detect and impossible to quantify without the image registration and measurement strategy described herein.

While the example discussed above concerned mapping retinal circulation, the methods disclosed herein can equally well be applied to assessing other medical conditions of the retina, such as artery occlusion, retinal detachments, and the size and distribution of inflammatory lesions or intraocular tumors.

It is apparent, therefore, that the disclosed subject matter improves over the prior art with regard to retinal imaging. Although the present disclosed subject matter has been described in detail, it should be understood that various changes, substitutions, and alterations may be readily ascertainable by those skilled in the art and may be made herein without departing from the spirit and scope of the present disclosed subject matter as defined by the claims. The foregoing description of specific embodiments of the disclosed subject matter has been presented for purposes of illustration and description. It is not intended to be exhaustive or to limit the disclosed subject matter to those embodiments disclosed. Thus, it is intended that the disclosed subject matter includes modifications and variations that are within the scope of the appended claims and their equivalents.

I claim:

1. A method for creating a widefield image of a retina in an eye, the retina being substantially spherical and internally having a posterior area and a plurality of peripheral areas, the peripheral areas each having a posterior portion disposed proximate the posterior area, comprising:
    taking a photographic base image of the posterior area;
    taking a photographic peripheral image of the peripheral areas;
    transforming the peripheral images using elastic deformation so that the posterior portions of the peripheral images substantially match the corresponding portions of the base image;
    warping each peripheral image to fit the base image; and
    montaging the warped peripheral images with the base image to form the widefield retinal image.

2. The method of claim 1, further comprising selecting common control points in each peripheral image and the base image.

3. The method of claim 2, wherein the selection of common control points is performed semi-automatically.

4. The method of claim 2, wherein the selection of common control points is performed manually.

5. The method of claim 2, further comprising superimposing the respective control points in the base and peripheral images.

6. The method of claim 1, wherein at least one peripheral image is warped using a transformation.

7. The method of claim 6, wherein the transformation employs thin-plate splines.

8. The method of claim 1, further comprising taking a plurality of photographic base images of the posterior area and selecting the base image with the best sharpness and lack of systemic distortion across the image.

9. The method of claim 1, further comprising taking a further plurality of photographic peripheral images, and selecting the peripheral images with the best sharpness and lack of systemic distortion across the image.

10. The method of claim 1, further comprising editing the posterior image and peripheral images to remove image artifacts from the lids, lashes and nose.

11. The method of claim 1, further comprising padding the posterior and peripheral images at their borders with additional black pixels.

12. The method of claim 1, further comprising inspecting the base and peripheral images to identify vortex vein ampullae;
    plotting the locations of the vortex vein ampullae onto the montaged widefield retinal image;
    providing a retinal schematic based on observed anatomic dimensions of the retina;
    plotting ocular landmarks, including the optic nerve, macula and equator onto the schematic warping of the montage image to fit the schematic using said landmarks.

13. The method of claim 12, further comprising transforming the warped montage image such that each pixel of the image corresponds to the same amount of retinal surface area.

14. The method of claim 12, further comprising applying a correction factor to calculate the area represented by a pixel in the montage image to the actual corresponding area of the retina as a function of radial distance from the center.

15. A widefield retinal image recorded on a tangible medium which has been created by the method of claim 1.

16. A method of diagnostic examination of a retina comprising examining a widefield retinal image in accordance with claim 15.

17. The method of claim 16, wherein said examination is an examination of circulatory and structural features visible from said widefield retinal image.

* * * * *